United States Patent [19]

Salam

[11] 4,449,934
[45] May 22, 1984

[54] PLAQUE REMOVER
[75] Inventor: Hassan P. A. Salam, London, England
[73] Assignee: Unisplay, S.A., Geneva, Switzerland
[21] Appl. No.: 318,237
[22] Filed: Nov. 4, 1981
[51] Int. Cl.³ .............................................. A61C 17/00
[52] U.S. Cl. ...................................... 433/143; 132/93
[58] Field of Search ........................... 433/143; 132/93; 15/111

[56] References Cited

U.S. PATENT DOCUMENTS

| | | | |
|---|---|---|---|
| 1,468,125 | 9/1923 | Nielsen | 132/93 |
| 1,658,706 | 2/1928 | Carrott | 15/111 |
| 1,796,367 | 3/1931 | Grove | 132/84 |
| 3,050,072 | 8/1962 | Diener | 132/93 |

FOREIGN PATENT DOCUMENTS

| | | | |
|---|---|---|---|
| 121867 | 7/1946 | Australia | 15/14 |
| 2487189 | 1/1982 | France | 433/143 |
| 99875 | 6/1923 | Switzerland | 132/93 |

Primary Examiner—Robert Peshock
Attorney, Agent, or Firm—Pollock, Vande Sande and Priddy

[57] ABSTRACT

A tooth cleaning instrument mounted at one end of a handle comprising a tapered blade of plastics material having a blunt apex folded about a base to apex line and inclined to the axis of the handle, the arrangement allowing all outer surfaces of the teeth as well as the spaces between them to be scraped to remove plaque and tartar. The other end of the handle can include a brush.

29 Claims, 11 Drawing Figures

PLAQUE REMOVER

FIELD OF THE INVENTION

This invention relates to an instrument for cleaning teeth and in particular for removing dental plaque and tartar therefrom.

BACKGROUND OF THE INVENTION

The toothbrush is the most widely used instrument for cleaning teeth, but there are certain areas of the teeth that it does not clean properly. These are at the gaps between the teeth and the surfaces of the teeth close to the gum line where there is a shallow pocket formed by the junction of the gum and tooth. Plaque tends to accumulate in these areas providing a bacteriological environment which irritates the gun and attacks the tooth, leading to caries. Irritated gums can become swollen, causing a deeper pocket between gum and tooth to form which in turn results in more plaque accumulated. This latter situation is very difficult to correct with a toothbrush as it cannot reach into the pocket and also at this stage the gum is sore and liable to bleed. Problems of gum inflammation are particularly prevalent in older people and are a major cause of loss of teeth.

Dental floss is used as a plaque remover but it has limitations and disadvantages. Its main use is to remove plaque accumulating in the gaps between the teeth using a shaving or scaling action with the floss slid into the intertooth gap, tensioned and pulled along the side of the tooth starting from the gum line in the direction away from it. If there is no gap between the crowns of the two teeth, the floss cannot easily be slipped in. It can be forced in, but there is the danger in doing so of injuring the gum. Dental floss cannot deal with the gum line pockets on the sides of the teeth facing the tongue and the cheek.

Another problem that can cause loss of teeth is accumulation of tartar round the tooth close to the gum line. Tartar tends to be hard, and brushes and dental floss are not suited to removing it. It needs to be gently chiselled off, and none of the instruments available to the general public provides this function.

SUMMARY OF THE INVENTION

The present invention provides an instrument that can remove plaque from all surfaces of the teeth. It can also be used to remove tartar before it builds up to a thick layer. The instrument is safe enough to be used by children. It is easy to use even for cleaning areas that are normally difficult to clean, such as the backs of the front teeth, the gaps between the teeth and the backs of the widsom teeth as well as sides of the teeth. The instrument has the advantage that the plaque removed can be seen clearly.

Broadly stated the invention provides an instrument suitable for removing plaque from teeth comprising a tapered blade which has a stiffening fold or curvature along a base to apex direction secured or securable to one end of an elongate handle with said direction of folding or curving of the blade being at an angle to the longitudinal axis of said handle, said fold or curvature extending from the base of said blade and said base being supported so as to maintain said fold or curvature, edges of said blade in use scraping plaque off the surfaces of the teeth, the blade being arranged to resist buckling when subjected to forces at its edges normal to its surface arising from said scraping.

In a preferred aspect of the invention the angle at the apex of the blade of points on the two opposed edges of the blade each 7 millimeters from the apex of the blade is greater than 15 degrees and also the blade is at least 0.15 mm wide at a distance 0.1 mm behind its apex. With this combination of dimensional features the blade is less sharply tapering than is normal in a conventional toothpick which is made long and pointed so as to be pushed longitudinally and penetrate between pairs of teeth, and it ends in a blunt broad and preferably radiused end that is less likely to puncture the gum if abused.

The instrument is best used after brushing in the normal way, and in an embodiment of the invention it is part of a toothbrush. This is for convenience and to encourage the user to do both brushing and scaling when cleaning the teeth. A few strokes with the plaque remover after brushing shows a significant amount of plaque on it and this indication makes the user appreciate that brushing alone is inadequate and provides an incentive for proceeding with scaling.

BRIEF DESCRIPTION OF DRAWINGS

Embodiments of the invention will now be described, by way of example only, with reference to the accompanying drawings, in which.

DETAILED DESCRIPTION OF ILLUSTRATED EMBODIMENTS

Figure 1:
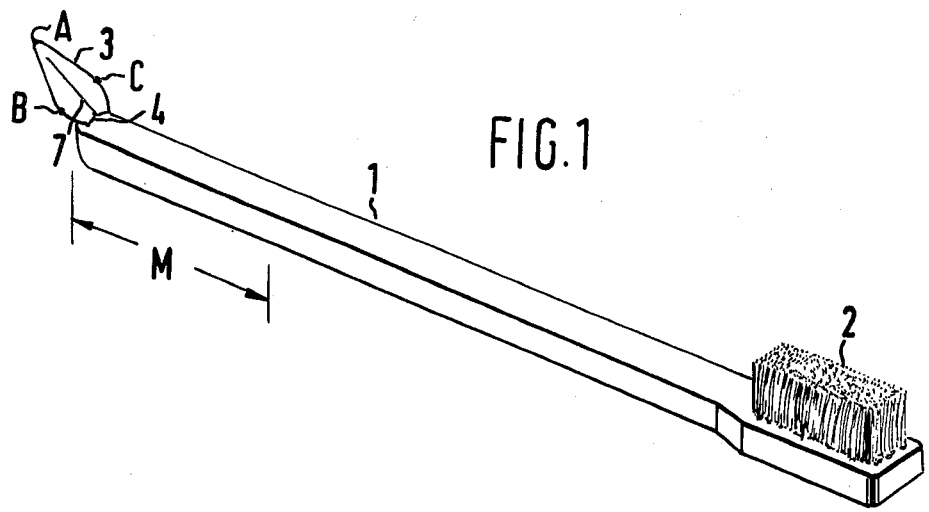
FIG. 1 is a perspective view of a combined toothbrush and plaque remover.

In FIG. 1, a tooth cleaning instrument comprises an elongate handle member 1 with a brush 2 at one end and a plaque remover 3 at the other. Plaque remover 3 comprises a blade of folded flexible non-toxic sheet-like plastics material arranged to remove plaque by a scraping or shaving action. A portion M of elongate member 1 of about four centimeters in length can be inserted in the mouth so that plaque remover 3 can be inserted in the mouth to reach the back teeth. This portion need not necessarily be parallel to the remainder of member 1. Plaque remover 3 can be integral with member 1 or a separate part that is fitted to it.

Figure 3:
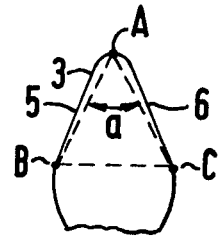
FIG. 3 is a view on an enlarged scale of the tip of the plaque removing blade in a flattened state.
Figure 4:
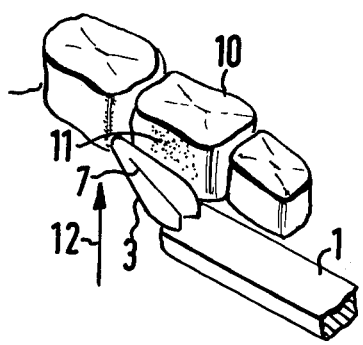
FIG. 4 is a view of the plaque removing end of the toothbrush scraping plaque off molar teeth.

FIG. 3 shows the shape of the blade when flattened. It has a blunt tip ending at a point "A" and two sides 5 and 6. FIG. 4 illustrates one mode of using the implement in which a side of blade 3 is used to shave plaque 11 off tooth 10 by moving it from the gum line in the direction of arrow 12 away from the gum. Alternatively the tip "A" of blade 3 can be used to shave or scoop off plaque from the sides of the teeth.

Figure 6:
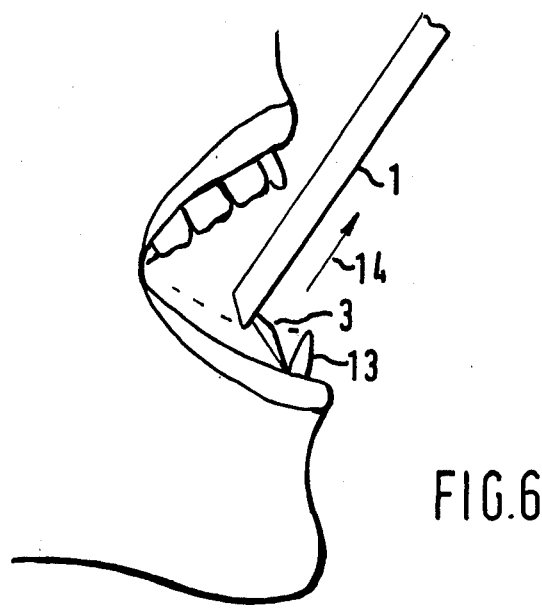
FIG. 6 illustrates a further manner of using the plaque removing end of the toothbrush.

FIG. 6 shows how the plaque remover can be used to remove plaque or tartar from the back of a lower incisor 13. The implement is moved in the direction of arrow 14 causing plaque and tartar to be chiselled off. The shaving action applies pressure to the edge of the blade normal to its surface tending to buckle the blade. To prevent such buckling at least part of the blade must be sufficiently broad and the blade must be curved or folded in this part.

Referring to FIG. 3 "B" and "C" are points on sides 5 and 6 respectively each 7 mm away from tip point "A". To prevent buckling the angle "a" of triangle BAC must exceed 15 degrees, and is preferably between 30 and 50 degrees. The portion BC is made wider than the base of the blade so that the edges of the blade near points B and C protrude out sideways enabling the lateral mid-regions of the blade also to be conveniently used for shaving.

In FIG. 1 the blade 3 is shown folded or curved about a central base-apex line 7 to form a channel or valley which extends along line 7 between sides 5 and 6. The fold extends into the portion of the blade between BC and the tip and is preferably continued right up to or close to the tip. The fold is permanently maintained in the blade by means more rigid than the portion between BC and the tip. In the embodiment in FIG. 1 the fold is permanently maintained by extending it in that portion of the blade that joins with member 1, as indicated by interface line 4. It is preferable to have the blade folded with a small radius less than 0.5 mm, or abruptly as shown at 7, rather than have it curved uniformly from B to C, so as to provide maximum resistance to bending and buckling of the line of material from the center of the base to the apex.

Figure 7:
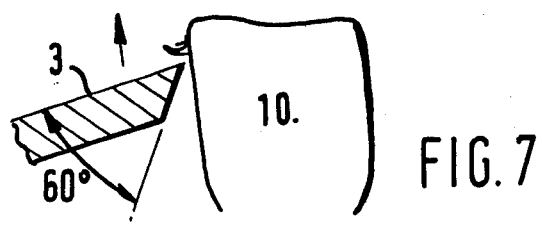
FIG. 7 is a view of an edge of the blade in section on an enlarged scale.

The mean thickness of the blade portion from line BC up to the tip "A" is between 0.12 and 0.35 mm, with 0.12 to 0.25 preferred, as this gives good stiffness without preventing the tip of the blade from unfolding temporarily when slipped into gaps between the teeth that are as narrow as 0.3 mm or thereabouts. The thickness of the blade can be less at the tip and at edges 5 and 6 than it is at the center of triangle BAC to facilitate insertion into narrow gaps. If desired the edges of the blade may be formed so as to present an acute-angled chiselling edge to the tooth surface as shown in the cross-sectional view of the blade in FIG. 7 to enhance the shaving action. The plaque remover 3 can be made as an integral part of handle 1 by injection moulding.

Any appropriate blade material may be used, but it is desirable to select a material which is appropriately durable and is not as hard as tooth enamel so as to minimize cumulative wear damage to the tooth surface and has low moisture absorption. The blade can be of a polyester, preferably polyester based on polyethylene terephthalate.

Figure 2:
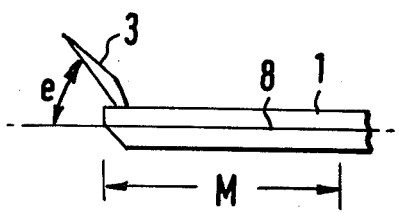
FIG. 2 is a side view of the plaque removing end of the toothbrush.

FIG. 2 shows a side view of the instrument. Blade 3 is set at an axillary angle "e" relative to the longitudinal axis 8 of portion M. This angle is greater than 25 degrees and preferably between 35 and 85 degrees.

The tip of the blade is made blunt in profile to avoid injury to the gums, and it is advantageous to make it wide so that it can remove more plaque and tartar per stroke.

Figure 5:
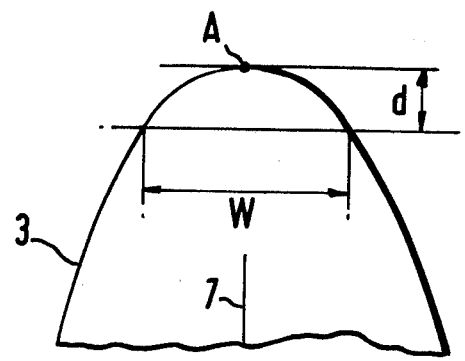
FIG. 5 is a view of the tip of the plaque removing blade on a further enlarged scale.

FIG. 5 shows the tip of a blade. For the purposes of this invention the tip is blunt if the width W of the blade at a distance $d = 0.1$ mm in from the extremity of the tip towards the support of the blade is greater than 0.15 mm. For implements for use by adults W is preferably between 0.3 and 0.8 mm and for those for use by children W is preferably between 0.6 and 1.2 mm.

Figure 10:
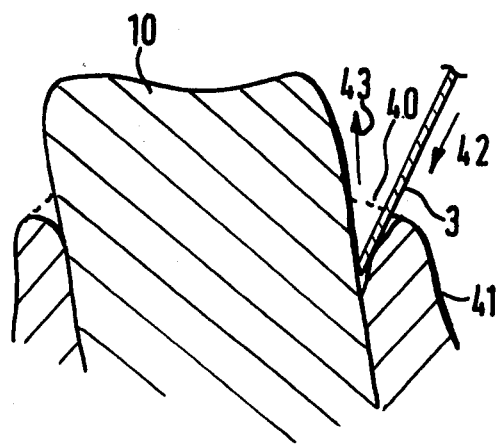
FIG. 10 shows in cross-section part of a tooth and gum with the tip of a blade according to the invention removing plaque from a gum pocket.

As illustrated in FIG. 10, the blunt tip or a portion of the blade 3 a little to the side of it can be used to gently spoon plaque and food debris 40 out of a pocket formed between a tooth 10 and adjacent swollen gum. The blade is inserted into the pocket in direction 42 to press against the side of the tooth and then moved away from the gum in the direction of arrow 43 to spoon out the unwanted matter and scrape the side of the tooth clean.

The instrument in FIG. 1 can be manufactured in two parts, one comprising the plaque remover and the other the brush. The two can be joined permanently or in a way that allows separation so that the plaque remover or the brush can be replaced.

Figure 8:
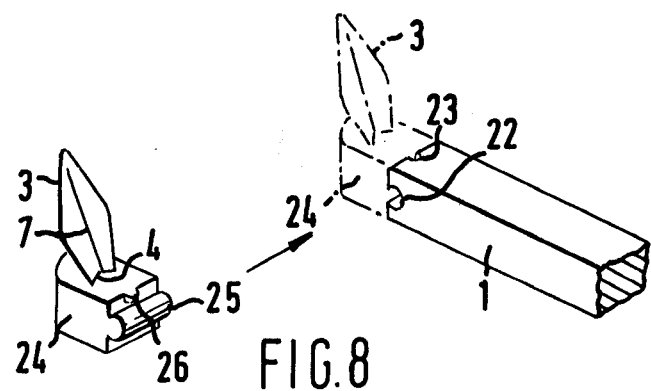
FIG. 8 shows a further embodiment in which the blade is provided in a demountable support that fits on the end of a toothbrush handle.

FIG. 8 shows an embodiment of the invention in which blade 3 is part of a replaceable blade-module 24 which can be inserted into and removed from an end of handle 1 the other end of which preferably includes a brush. Blade-module 24 includes a tongue portion 25 which fits into a corresponding groove 22 in handle 1. It also includes a small protrusion 26 which snaps into a corresponding small cavity 23 in handle 1 to keep the blade-module 24 securely attached to the handle when fitted to it. The blade-module can be made of plastics material. The other end of the handle could be arranged to receive another blade module where the blade is directed at a different angle as described below with reference to FIG. 11.

Figure 9:
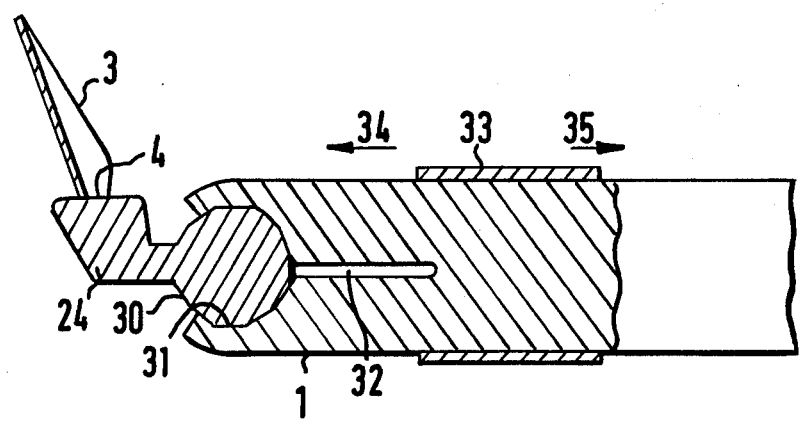
FIG. 9 shows a second embodiment of a blade on a demountable support.

FIG. 9 shows a sectional view of another embodiment using a replaceable blade-module 24 including a plaque shaving blade 3 and a ball portion 30 having multiple planar facets which fits into a corresponding multifaceted spherical socket 31 in handle 1. Blade-module 24 can be rotated about 3 axes to provide adjustment of the angle of the blade relative to the handle. A tubular collar 33 around the handle is provided which can be moved towards the ball and socket arrangement, which is arranged when the collar is over it to be locked so that the blade position does not alter inadvertently. Handle 1 is bifurcated at 32 to allow replacement of blade-module 24 when collar 33 is withdrawn in direction 35. The other end of the handle not shown can include a brush.

Figure 11:
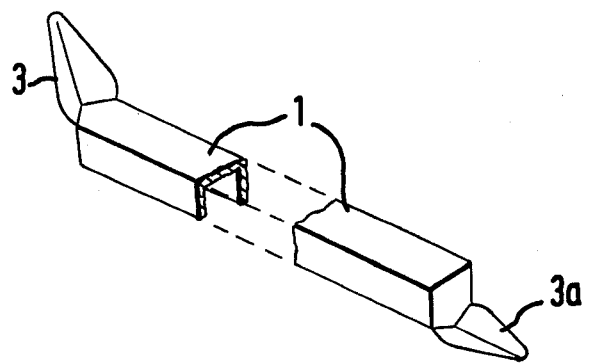
FIG. 11 is a view of a double ended plaque removing device.

FIG. 11 shows a disposable plaque and tartar remover according to the invention. It includes a handle 1 with a hollow structure that is open underneath. A first plaque removing blade 3 is fixed to one end of the handle and is set at an angle relative to the longitudinal axis of the handle as previously described. A second plaque removing blade 3a roughly in line with the axis of the handle is fixed at the other end. The handle and the two blades may be moulded together as one piece. Blade 3a can be used for scraping the outer sides of the front teeth and preferably has the same design characteristics as blade 3, to provide the desired stiffness, safety and shaving efficiency.

The construction of blade 3 and its support at its base for the embodiments in FIGS. 8, 9 and 11 is the same as was described in relation to FIGS. 1, 2, 3, 5 and 7.

For all embodiments the blade is preferably arranged to have an appearance other than white, so that plaque accumulating on it can be seen easily. The blade can be transparent and colorless for this purpose.

Various modifications may be made to the embodiment shown without departing from the invention, the scope of which is defined in the appended claims. For example, the instrument can be made simply as a plaque remover without the brush, or with the brush replaced with a different type of tooth cleaner.

I claim:

1. An instrument for removing plaque from natural teeth, comprising:
 a member arranged to replaceably fit onto a handle;
 a blade of thin flexible sheet-like material tapering in width from a base portion to an apex, said blade being stiffened by having a fold forming a valley extending along the direction from said base portion to said apex;
 means securing said blade to said member arranged so that said blade extends away from said member and arranged to maintain said fold at said base portion;
 the combination of said blade and said member being compact in the direction in which said blade extends away from said member facilitating placement of said combination in the mouth for scraping the back surfaces of the front teeth and each side surface of each of the other teeth, said blade and said securing means being arranged to resist buckling when said blade is subjected to forces in the direction onto its concave side normal to its surface arising from said scraping.

2. An instrument according to claim 1, wherein said sheet-like material constituting said blade is less than 0.35 millimeters thick so as to yield and conform to the shape of and so as to enter into narrow gaps between the teeth, and furthermore wherein the angle at said apex of points on two opposed edges of said blade each 7 millimeters from said apex is greater than 15 degrees, measured when the sheet-like material of said blade is flattened, so as to provide resistance to buckling of said blade.

3. A device for cleaning natural teeth comprising an instrument as claimed in claim 1, and an elongate handle having a brush at one end and adapted at the other end to have fitted thereto said member of the instrument in such manner that said blade projects away from said handle at an angle exceeding 25 degrees relative to the longitudinal axis of said handle.

4. A device for cleaning natural teeth comprising an instrument as claimed in claim 2 and an elongate handle having a brush at one end and adapted at the other end to have fitted thereto said member of the instrument in such manner that said blade projects away from said handle at an angle exceeding 25 degrees relative to the longitudinal axis of said handle.

5. A device according to claim 3, wherein said angle at which said blade projects is adjustable.

6. An instrument according to claim 1, wherein said apex of said blade is blunt for safety and to assist removal of plaque by said apex, and wherein said blade is of a color contrasting with white whereby removed plaque can be seen clearly.

7. An instrument according to claim 1, wherein said blade is transparent and colorless.

8. An instrument according to claim 1, wherein said blade is of polyester-type plastics material.

9. An instrument according to claim 1, wherein said securing means is of smaller width than said base portion.

10. An instrument according to claim 1, made integrally of plastics material.

11. An instrument according to claim 1, and arranged to snap fit onto a handle.

12. An instrument according to claim 1, wherein said blade includes an outer edge surface forming an acute angle with the concave surface of said folded blade.

13. An instrument for removing plaque from natural teeth, comprising:
 an elongate handle;
 first and second blades of thin flexible sheet-like material each tapering in width from a base portion to an apex, each said blade being stiffened by having a fold forming a valley exrending along the direction from said base portion to said apex, said blade being pliant compared with said handle;
 means arranged to secure each of said blades to a respective end of said handle, at least one of said blades projecting away from said handle at an angle exceeding 25 degrees relative to the longitudinal axis of said handle, said securing means being arranged to maintain said fold at said base portion;
 the combination of said projecting blade and said handle being compact in said projecting direction thereby facilitating placement of said blade in the mouth for scraping the back surfaces of the front teeth and each side surface of each of the other teeth, said blade and said securing means being arranged to resist buckling when said blade is subjected to forces in the direction onto its concave side and normal to its surface arising from said scraping.

14. An instrument according to claim 13, wherein said handle is hollow and open along a longitudinal side.

15. An instrument according to claim 13, wherein at least said handle and one of said blades are together formed as a single member out of plastics material.

16. An instrument for removing plaque from natural teeth, comprising:
 an elongate handle;
 a blade of thin flexible sheet-like material tapering in width from a base portion to an apex, said blade being stiffened by having a fold forming a valley extending along the direction from said base portion to said apex, said blade being pliant compared with said handle;
 means arranged to secure said blade to an end of said handle with said blade projecting away from said handle at an angle exceeding 25 degrees relative to the longitudinal axis of said handle, said securing means being arranged to maintain said fold at said base portion;
 the combination of said blade and said handle being compact in said projecting direction thereby facilitating placement of said blade in the mouth for scraping the back surfaces of the front teeth and each side surface of each of the other teeth, said blade and said securing means being arranged to resist buckling when said blade is subjected to forces in the direction onto its concave side and normal to its surface arising from said scraping.

17. An instrument according to claim 16, wherein said sheet-like material constituting said blade is less than 0.35 millimeters thick so as to yield and conform to the shape of and so as to enter into narrow gaps between the teeth, and further more wherein the angle at said apex of points on two opposed edges of said blade each 7 millimeters from said apex is greater than 15 degrees, measured when the sheet-like material of said blade is flattened, so as to provide resistance to buckling of said blade.

18. An instrument according to claim 16, wherein the end of said handle opposite to that securing said blade is formed as a toothbrush.

19. An instrument according to claim 17, wherein the end of said handle opposite to that securing said blade is formed as a toothbrush.

20. An instrument according to claim 16, wherein said apex of said blade is blunt for safety and to assist removal of plaque by said apex.

21. An instrument according to claim 17, wherein said blade is of a color contrasting with white whereby removed plaque can be seen clearly.

22. An instrument according to claim 21, wherein said blade is transparent and colorless.

23. An instrument according to claim 16, wherein said blade is of polyester-type plastics material.

24. An instrument according to claim 16, wherein said securing means is of smaller width than said base portion.

25. An instrument according to claim 18, wherein said sheet-like material constituting said blade is between 0.12 and 0.25 millimeters thick.

26. An instrument according to claim 16, wherein the radius of said fold is less than 0.5 millimeters.

27. An instrument according to claim 19, wherein said angle at said apex is between 30 and 50 degrees.

28. An instrument according to claim 16, wherein said angle at which said blade projects is between 35 and 85 degrees.

29. An instrument according to claim 16, wherein said angle at which said blade projects is adjustable.

* * * * *